United States Patent [19]

Degrave

[11] Patent Number: 4,595,563
[45] Date of Patent: Jun. 17, 1986

[54] APPARATUS FOR SAMPLE TRANSFER AND ANALYSIS BY CENTRIFUGATION

[75] Inventor: Philippe L. Degrave, Viroflay, France

[73] Assignee: Kontron Holding A.G., Zurich, Switzerland

[21] Appl. No.: 733,285

[22] Filed: May 10, 1985

[30] Foreign Application Priority Data

May 11, 1984 [CH] Switzerland ............ 2339/84
Aug. 14, 1984 [CH] Switzerland ............ 3894/84

[51] Int. Cl.$^4$ .............. G01N 21/01; G01N 35/02; G01N 21/84
[52] U.S. Cl. .................. 422/72; 356/426; 356/427; 422/63; 422/64; 422/102; 422/104; 424/16; 424/20
[58] Field of Search ............ 494/16, 19, 20; 422/63, 422/64, 72, 102, 104; 356/246

[56] References Cited

U.S. PATENT DOCUMENTS

| 3,532,470 | 10/1970 | Rochte ............ 422/61 |
| 3,750,941 | 8/1973 | Drucker ............ 494/16 |
| 3,762,635 | 10/1973 | Hankey ............ 494/16 |
| 4,010,892 | 3/1977 | Revillet et al. ............ 494/16 |
| 4,193,536 | 3/1980 | Kuboto ............ 494/16 |
| 4,201,335 | 5/1980 | Conn et al. ............ 422/72 |
| 4,236,666 | 12/1980 | Aeschlimann et al. ............ 422/72 |

FOREIGN PATENT DOCUMENTS

| 2201542 | 4/1973 | Fed. Rep. of Germany ........ 494/16 |
| 846439 | 8/1960 | United Kingdom ............ 424/16 |

Primary Examiner—Michael S. Marcus
Attorney, Agent, or Firm—Jon S. Saxe; Bernard S. Leon; George M. Gould

[57] ABSTRACT

Apparatus for sample transfer and analysis by centrifugation, comprising a rotor having rotary joints at its periphery, to which cuvette carriers are connected so as to be able to perform a tipping movement through an angle of 90°, a locking device for locking the cuvette carriers in an inclined position, and cuvette assemblies for use in the cuvette carriers, the rotor preferably being in the form of a rotary beam at the two ends of which two cuvette carriers are disposed, and the cuvette carrier is in the form of a comb so that the teeth engage between the cuvette rows of the cuvette assembly. This apparatus enables samples to be transferred without mixing the cuvette contents.

9 Claims, 5 Drawing Figures

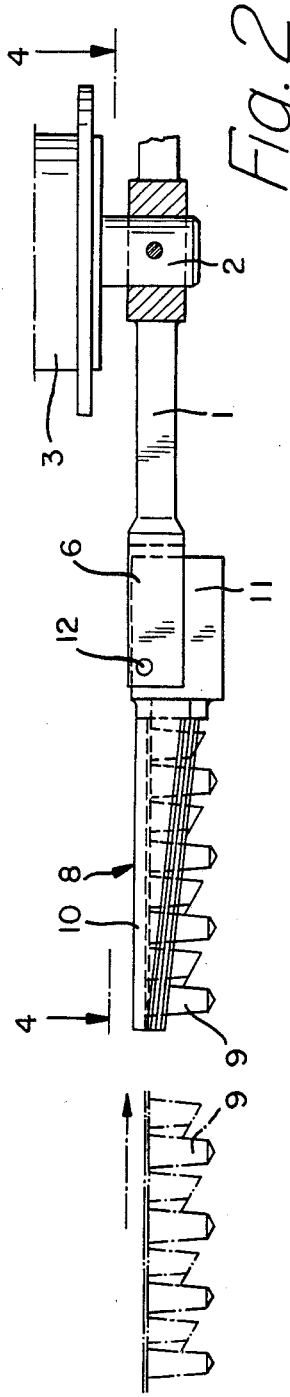
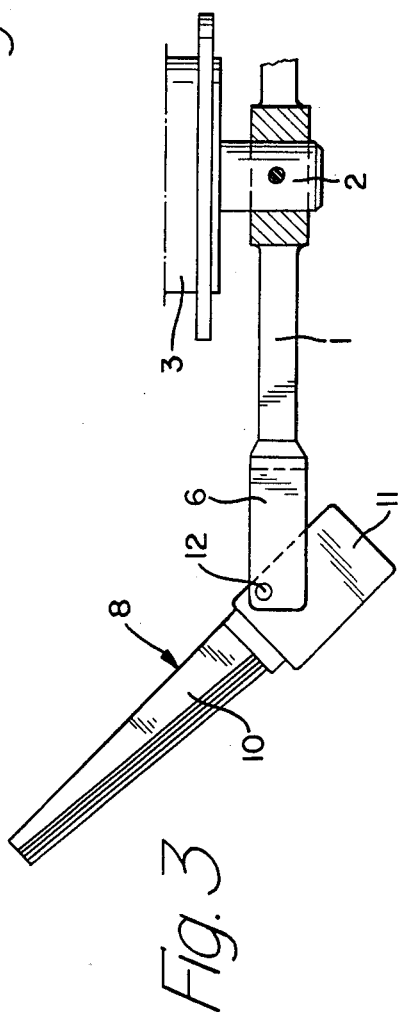
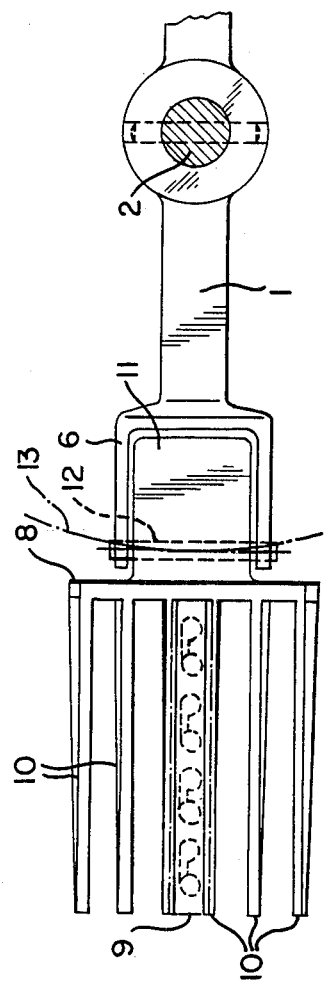

APPARATUS FOR SAMPLE TRANSFER AND ANALYSIS BY CENTRIFUGATION

DETAILED DESCRIPTION OF THE INVENTION

The invention is concerned with an apparatus for sample transfer and analysis by centrifugation.

Automated analyzers are being increasingly used in chemical, biochemical and medical analyses. Many of them operate according to a method in which centrifugation is carried out in one or more stages or phases of the analytical procedure. Centrifugations are used in this case mainly for the following purposes:

1. To transfer samples from a group of cuvettes or sample chambers, into which the samples to be investigated and the reagents are first introduced separately, into a second group of cuvettes or chambers in which samples and reagents are mixed, the reaction required for the determination can take place and finally the measurement is carried out. The real advantage of this sample transfer by centrifugation is that a plurality of samples are simultaneously brought together with the corresponding reagents so that so-called dynamic measurements can be carried out based on the defined time for the plurality of samples. The analyzer of N. G. Anderson, which is described, for example, in German Auslegesschrift No. 1 900 275, is the first system of this kind.

2. Another purpose for which a centrifugation step is usually used in analyzers is the actual classical centrifugation, i.e. the rapid separation of phases which would not take place or would take place only very slowly by acceleration due to gravity. Such phase separations are carried out primarily in the case of agglutination reactions of the kind which are gaining increasing significance, primarily in immunological diagnostics.

3. A third purpose of centrifugation is to differentiate between a positive and negative reaction in a method for the determination of antigens or antibodies etc, in a biological sample in accordance with German Offenlegungsschrift No. 29 07 198. In this method, the cells which have reacted negatively and accordingly do not adhere to a protein layer covering the base of a U- or V-shaped cuvette are separated by centrifugation and collected at the lowest point of the cuvette, while in the case of a positive reaction the cells adhere due to immunological bonding forces and are not separated by the same centrifugal force.

In the case of immunological diagnostic methods, another factor in addition to the aspect of phase separation in centrifugation is that the high acceleration during centrifugation also provides the necessary contact between the individual reaction partners more rapidly and better than would be the case solely by acceleration due to gravity. Another factor to be taken into account in the case of immunological diagnostic methods is that these methods do not simply comprise bringing together a sample and a reagent as in previous analyses, but instead an entire series of alternating washing operations and reagent additions is frequently required. This more complex combination of method steps unavoidably leads to more complicated equipment which permits this sequence of method steps. A typical example of such a relatively complicated apparatus is the centrifugation device described in German Offenlegungsschrift No. 29 07 823. This device is so designed that a plurality of consecutive so-called washing operations is possible.

As an alternative to the method comprising a plurality of washing operations, a method is also known in which the constituent of interest in the sample, i.e. for example the antigen/antibody complex, can be diffused through a purification layer, for example of an albumin. This diffusion is advantageously accelerated by centrifugation. It is a prerequisite in the performance of this method that the sample should be disposed in a layer on the purification layer so that it can not come directly into contact with the coating on the base of the cuvette. It was hitherto possible to carry out this method only by introducing the sample over the albumin layer manually and then carrying out centrifugation in a centrifuge with a swingout rotor. None of the known automatic analyzers is suitable for this method, because they basically involve mixing during the sample transfer by centrifugation, and this is what must be avoided under all circumstances in the method in question.

The object of the invention is to provide an apparatus for sample transfer and analysis by centrifugation, by means of which sample transfer from one chamber to another can be so carried out that no mixing takes place. Another object of the invention is to provide an apparatus which, although suitable for the performance of complex immunological analytical methods, is simple and inexpensive not only with respect to its manufacture but also with respect to its use, i.e. the consumption of disposable cuvettes.

This is achieved in accordance with the invention by an apparatus of the type referred to hereinbefore, which is characterized by the combination of a drive system with a motor, a rotor which can be rotated by the drive system and which extends symmetrically radially outwards from its centre connected to the drive system and which at its periphery has rotary joints, cuvette carriers connected to the rotary joints so as to be able to carry out a tipping movement about a tangent to a turning circle described by the joints during centrifugation, as the tipping axis, the tipping movement including an angle of 90° and the cuvette carriers being suspended so that the part of the mass situated inside the turning circle is greater than that outside the turning circle, a locking device for locking the cuvette carriers in an inclined position, and cuvette assemblies for use in the cuvette carriers.

One exemplified embodiment of the invention is described hereinafter on the basis of the accompanying drawing in which:

FIG. 2 shows a rotary beam having a cuvette carrier and a cuvette assembly in the non-operating position;

FIG. 3 shows a rotary beam having a cuvette carrier without a cuvette assembly in the non-operating position;

FIG. 4 shows a section along line IV—IV in FIG. 2;

Figure 1:
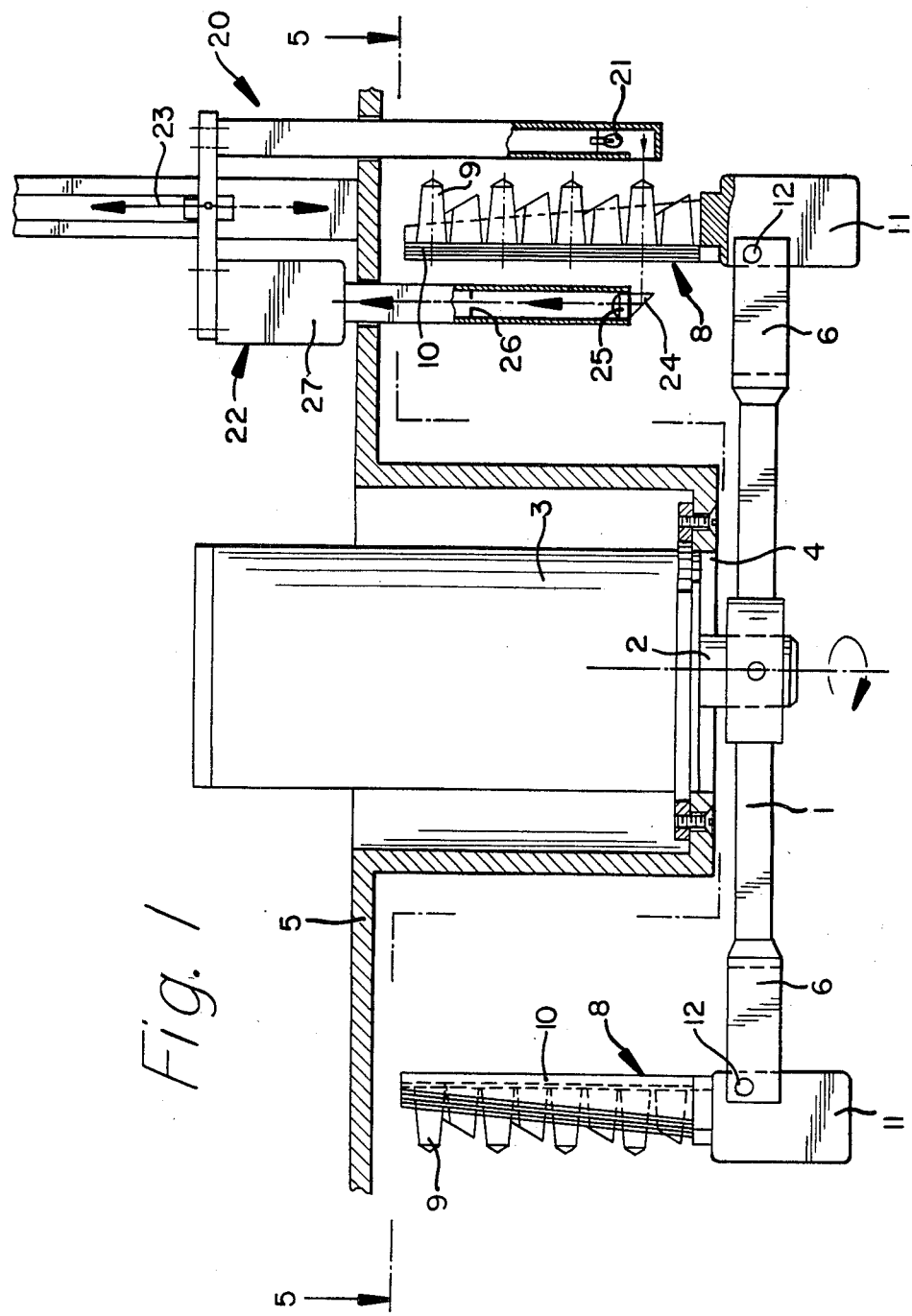
FIG. 1 shows an apparatus in accordance with the invention during the centrifugation, partly in section.

A rotary arm or rotary beam 1 is disposed symmetrically on the shaft 2 of a motor 3 which is in turn mounted in a recess in a housing 5 having an opening 4. In place of the arm or beam there is also possible another form of a rotor, for example a spider having four arms or a disc. The arm or beam 1 has a fork 6 at each of its two ends. A cuvette carrier 8 is disposed between the two prongs or tines of the forks 6 in each case.

As will be clearest from FIG. 4, the cuvette carrier 8 has a comb-like form with teeth 10 and a back 11 of relatively large dimension. The comb-shaped cuvette carrier 8 is connected to the fork tines by bolts 12 so as to be pivotable about the axis defined by the bolts 12, said axis coinciding with a tangent to the turning circle 13 described by the joint during centrifugation. The cuvette carrier 8 is dimensioned so that the back part 11 projecting towards the axis of rotation of the motor beyond the bolt pivot axis is heavier than the rest of the back and the teeth. As a result, no external forces are required, i.e., solely by the effect of gravity the sample carrier can always be easily tipped up so that the teeth extend upwards at an angle (FIG. 3). During centrifugation, a greater centrifugal force acts on the heavy back part 11 so that the cuvette carrier 8 is fully projected upward as shown in FIG. 1.

The comb-like cuvette carrier 8 is used to receive a cuvette assembly 9 which basically has a similar construction to known and commercial microtitre plates. The teeth of the comb-shaped cuvette carrier and the spacing between them are of dimensions such as to engage in the gaps between the individual containers on the underside of the plates. For this purpose, however, unlike the commercial micro-titre plates, the side wall is either interrupted or completely omitted on one side of the plate.

Unlike the conventional micro-titre plates, the cuvettes are each grouped in pairs in the cuvette assembly 9 for the present apparatus, in such manner that each two cuvettes disposed side by side in the direction parallel to the teeth together form pairs. Between the two chambers of each pair there is a connection formed by the partition normally situated between the two cuvettes. This connection is provided by forming a recess in one connection so that a channel is formed between the two cuvettes of a pair to make the connection.

This description will not go into detail concerning the construction and function of the various embodiments of the cuvette assembly 9. For this purpose reference should be made to patent application Ser. No. 06/733,179 filed on even date herewith entitled Cuvette Assembly in the names of Ph. L. Degrave and J. Trouillet. For an understanding of this invention it is sufficient to refer to the above-described embodiment in which a channel-like connecting duct is provided between each two cuvettes of a pair. As a result of the arrangement of the two cuvettes of each pair this channel extends radially with respect to the axis of the driving motor.

An optical reading station 20 is provided to evaluate the result of the analysis, and consists basically of a light source 21 and a detector 22. The reading station also contains a feed mechanism by means of which the light source 21 and the detector 22 can be moved up or down stepwise. The mechanism for performing this stepwise movement is of conventional construction and not shown in detail. The movement is simply indicated by the arrow 23.

The light source 21 and the detector 22 are disposed so that the cuvette carrier 8 with the cuvette assembly 9 extends between the light source and the detector during centrifugation.

The light source 21 is constructed so as to provide uniform diffuse illumination of the area corresponding to one cuvette. The detector comprises a prism 24 to deflect the rays of light. A kind of lens comprising an optical system 25 and a gap 26 connects the prism 24 to a photomultiplier (secondary electron multiplier) 27, by means of which the light intensity of an imaged point is determined. The aperture 26 has a diameter of about 50 μm. The area corresponding to the base of the cuvette, or a part thereof, of the magnitude of about 1.5 mm diameter, can be scanned by a suitable choice of the optical system and by means of the diaphragm 26 so that the light intensity of about 1000 discrete points is covered. The lines of these raster points are obtained from the rotary movement and the scanning sequence, while the steps from one line to the next are effected by means of the mechanical advance.

The analysis comprises the following sequence. The cuvette assemblies are prepared outside the apparatus, i.e. samples and reagents are introduced into the cuvette assembly. One chamber of each pair is used to receive the sample-reagent mixture, namely the inner chamber, i.e. the one which is closer to the motor axis when the rotary arm is stationary. A layer of protein, for example an immunoglobulin, is applied to the base of the outer chamber, depending upon whether the addition does or does not take place after the reaction has taken place in the inner chamber. The outer chamber also contains a given quantity of a liquid which serves as a purification filter for the sample. An albumin, for example, is used for this purpose.

The thus-prepared, i.e. filled, cuvette assembly is placed on the cuvette carrier, and a second plate is placed on the second cuvette carrier. This can be carried out fully automatically by suitable mechanical means. To this end, the arm is secured at a loading station and the cuvette carrier is simultaneously brought into the horizontal position. In this position the cuvette assembly can be pushed on to the teeth of the cuvette carrier.

After the two cuvette assemblies have been fitted, the arm is rotated by the motor. The speed of rotation is initially slow and is selected so that the cuvette carriers assume an angle of about 45° to the horizontal. This angle can additionally be secured by providing a locking means (not shown). In this inclined position the sample flows, as a result of the centrifugal force, through the connecting channel from the inner chamber in each case to the outer chamber of a pair. The sample-reagent mixture occupies the position above the albumin layer without any mixing taking place. After the transfer of the sample-reagent mixture from each inner chamber to the outer chamber, the motor is accelerated—after the locking system has been released where applicable—and the actual centrifugation is carried out. During this procedure the antigen-antibody complex of interest migrates through the albumin layer and any unfixed antibodies are removed before the complex reaches the base of the cuvette. After the time required for this diffusion, the test is carried out as already described above.

Figure 5:
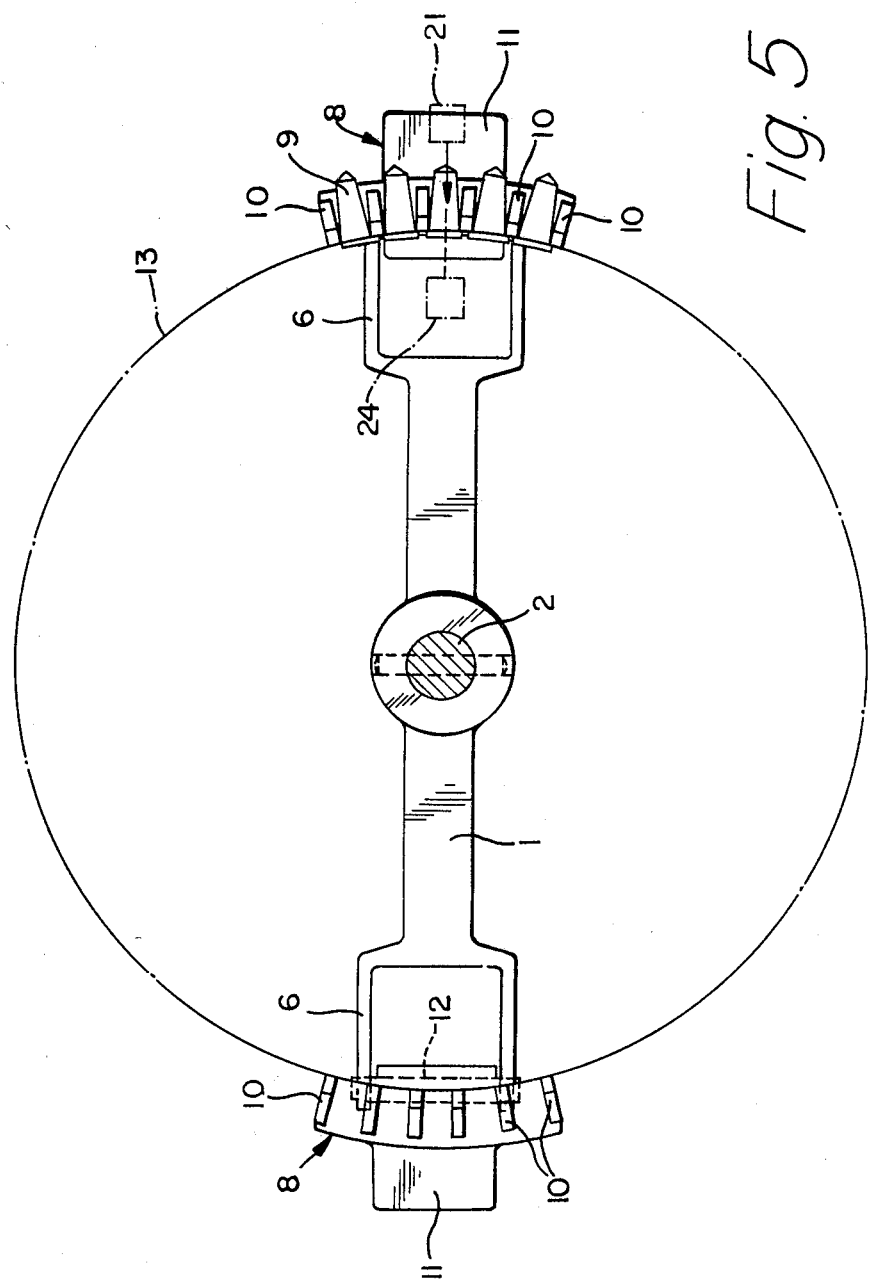
FIG. 5 shows a section along line V—V in FIG. 1.

Depending on the size of the cuvette assembly 9, it may be necessary for the cuvette carrier 8 to be wider than shown in FIG. 4. More particularly, it would be advantageous to use cuvette carriers having the same dimensions as conventional micro-titre plates. The advantage of this would be that sample preparation can be carried out using the same machines as used with micro-titre plates. However, if the cuvette assemblies are provided in that size, the cuvette carrier 8 must be curved according to the turning circle, as is best seen in FIG. 5, since otherwise the error due to differences in centrifugal force during centrifugation would be excessive. Of course, depending on the curvature of the cuvette carrier the cuvettte assembly must also be flexible so as to be adaptable to that curvature. However, there is no difficulty in achieving this construction. When narrow cuvette assemblies 9 are used, the difference in centrifugal force during centrifugation can be ordinarily disregarded in the case of a non-curved arrangement, and accordingly a simpler cuvette mounting can be used.

I claim:

1. An apparatus for sample transfer and analysis by centrifugation, comprising a drive system including a motor, a rotor connected to the drive system, said rotor having at least one arm extending radially from the connection of the rotor to the drive system, a cuvette carrier including a base portion and a cuvette carrying portion connected to said base portion, said cuvette carrying portion being adapted to receive a cuvette assembly, said base portion being pivotally connected to said arm at the end of said arm distal to said connection, said arms and said cuvette carrier being disposed along a substantially horizontal axis, the mass of the portion of the cuvette carrier situated between the pivotal and its distal end being less than the mass of the portion of the cuvette carrier situated between the pivotal connection and its end proximate the rotor whereby upon a first centrifugal speed, the cuvette carrier is tilted upwardly from the horizontal axis to one angle of inclination with respect to the horizontal axis at which inclination sample transfer can occur and upon increasing the rotational speed to a second rotational speed, to a second angle of inclination higher than the first with respect to said horizontal axis and at which sample analysis can occur and means for analyzing the sample at said second angle.

2. An apparatus as in claim 1 wheren the tilting movement occurs about a tangent to a turning circle described by the joints during centrifugation, as the tilting axis, the tilting movement including an angle of 90° and the cuvette carrier being suspended so that the part of the mass situated inside the turning circle is greater than that outside the turning circle.

3. An apparatus according to claim 1 wherein the distal end of the arm is fork-shaped and the cuvette carriers are positioned between the tines of the fork-shaped end.

4. An apparatus according to claim 1, wherein the rotor has two arms extending outwardly in two opposite directions from the center and at whose two ends two cuvette carriers are fitted.

5. An apparatus according to claim 4, wherein the distal ends of the arms are fork-shaped and the cuvette carriers are positioned between the tines of the fork-shaped ends.

6. An apparatus according to claim 1, wherein the cuvette carrier is shaped at its proximal end as a comb, the teeth of which are adopted to engage a cuvette assembly.

7. An apparatus acording to claim 6, characterized in that the cuvette carrier is curved transversely of the teeth to match the turning circle of the pivotal connection.

8. An apparatus according to claim 1, characterized in that the means for analyzing the sample comprising a light source and a light detector disposed for vertical displacement so that a cuvette carrier tilted up to the second angle passes between the light source and the light detector.

9. An apparatus as in claim 8 wherein the second angle is an angle of 90°.

* * * * *